United States Patent
Allen (10) Patent No.: US 10,696,994 B2
(45) Date of Patent: Jun. 30, 2020

(54) SIZE SELECTION OF RNA USING POLY(A) POLYMERASE

(71) Applicant: Bioo Scientific Corporation, Austin, TX (US)

(72) Inventor: Kevin Allen, Austin, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 0 days.

(21) Appl. No.: 16/145,911

(22) Filed: Sep. 28, 2018

(65) Prior Publication Data

US 2020/0102586 A1   Apr. 2, 2020

(51) Int. Cl.

| C12Q 1/6855 | (2018.01) |
|---|---|
| C12P 19/34 | (2006.01) |
| C12Q 1/686 | (2018.01) |
| C12N 9/12 | (2006.01) |
| C12Q 1/6848 | (2018.01) |
| C12Q 1/6869 | (2018.01) |

(52) U.S. Cl.
CPC ............ *C12P 19/34* (2013.01); *C12N 9/127* (2013.01); *C12N 9/1276* (2013.01); *C12Q 1/686* (2013.01); *C12Q 1/6848* (2013.01); *C12Q 1/6855* (2013.01); *C12Q 1/6869* (2013.01)

(58) Field of Classification Search
None
See application file for complete search history.

(56) References Cited

U.S. PATENT DOCUMENTS

| 2009/0042192 A1 | 2/2009 | Kiefer et al. |
| 2012/0208707 A1 | 8/2012 | Zeiner et al. |
| 2018/0265912 A1 | 9/2018 | Tian et al. |

FOREIGN PATENT DOCUMENTS

WO   WO 2015/173402 A1   11/2015

OTHER PUBLICATIONS

Wigley et al (Molecular and Cellular Biology 10:1705-13) (Year: 1990).*
Winters et al (JBC 248:4756-62) (Year: 1973).*
McDevitt et al (Genes & Development 2:588-97) (Year: 1988).*
Adiconis et al (Nature Methods 10:62329) (Year: 2013).*
Benes et al., "Expression profiling of microRNA using real-time quantitative PCR, how to use it and what is available", Methods, 2010, 50: 244-249.
Fu et al., "Identificaiton of human fetal liver miRNAs by a novel method", FEBS Letters, 2005, 579: 3849-3854.
Levin et al., "Comprehensive comparative analysis of strand-specific RNA sequencing methods", Nat Methods., 2010, 7(9): 709-715. doi:10.1038/nmeth.1491.
Shi et al., "Validation of artificial microRNA expression by poly(A) tailing-based RT-PCR", Protocol Exchange, 2012, doi:10.1038/protex.2012.003.
Lingner et al., "3'-end labeling of RNA with recombinant yeast poly(A) polymerase", Nucleic Acids Research, 1993, 21(12): 2917-2920.
Ying et al., "The MicroRNA (miRNA): Overview of the RNA Genes that Modulate Gene Function", Mol Biotechnol, 2008, 38: 257-268.

* cited by examiner

*Primary Examiner* — Christopher M Gross
(74) *Attorney, Agent, or Firm* — James S. Keddie; Bozicevic, Field & Francis LLP (57) ABSTRACT

This disclosure provides, among other things, a method for making a cDNA library. In some embodiments the method may comprise adding a polyA tail to the longer RNA fragments but not the shorter RNA fragments in a sample by incubating the population of RNA fragments with a polyA polymerase, wherein the reaction conditions used preferentially tail only the longer fragments but not the shorter fragments.

15 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 17
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (16)..(16)
<223> OTHER INFORMATION: v is G, A or C
<220> FEATURE:
<221> NAME/KEY: misc_feature
<222> LOCATION: (17)..(17)
<223> OTHER INFORMATION: n is a, c, g, or t

<400> SEQUENCE: 1
tttttttttt tttttvn                                                    17
```

SIZE SELECTION OF RNA USING POLY(A) POLYMERASE

BACKGROUND

Certain cDNA library preparation methods involve fragmenting mRNA and then reverse transcribing the resultant fragments of mRNA to make cDNA. In these methods, cleavage typically occurs at random or semi-random positions and, as such, the population of RNA fragments made by such methods typically contains RNA fragments of different lengths, wherein at least some of the fragments are relatively small, i.e., less than 20 nucleotides in length. These short fragments are problematic because their cDNA copies are amplified very efficiently but their sequences (particularly for fragment that are 10-15 in length) are not always uniquely mappable to a transcriptome. This problem can be potentially avoided by performing a physical size selection of the cDNAs or the amplification products. However, because of the imprecise nature of physical size selection methods it is impossible to eliminate cDNA copies of the shorter RNAs without also eliminating cDNA copies of many of longer RNAs, A better way for selecting RNA molecules by size is therefore needed.

SUMMARY

This disclosure provides, among other things, a method for processing an RNA sample. In some embodiments, the method may comprise: (a) fragmenting a sample comprising RNA (e.g., a sample that may comprise at least mRNA, e.g., at least mRNA and lncRNA) to produce a population of RNA fragments of different lengths, wherein the population of RNA fragments comprises longer RNA fragments and shorter RNA fragments, (b) incubating the population of RNA fragments with a polyA polymerase under conditions wherein the polyA polymerase preferentially adds a polyA tail to the longer RNA fragments and not the shorter fragments, to produce tailed RNA; (c) hybridizing the tailed RNA to an oligo(dT) oligonucleotide; and (d) reverse transcribing the tailed RNA using the oligo(dT) oligonucleotide as a primer to produce a cDNA library or enriching for the tailed RNA by washing away RNA molecules that are not hybridized to the oligo(dT) oligonucleotide.

The present method is based in part on the discovery that polyA polymerase has a preference for longer RNA substrates. This discovery can be applied in an in vitro polyadenylation reaction in order to polyadenylate only the longer RNA fragments and thereby eliminate shorter RNA fragments from future analysis. The preference of polyA polymerase for shorter substrates can be tuned by varying the reaction conditions. In many cases, limiting the activity of the enzyme in a polyadenylation reaction will result in the preferential polyadenylation of only the longer RNA fragments. This can be accomplished, for example, by reducing the amount of enzyme in the reaction, by reducing the amount of free $Mg^{2+}$ in the reaction, or by modifying other reaction conditions. The reaction conditions can be tuned so that RNA fragments that are at least 20 ribonucleotides in length are preferentially polyadenylated relative to the smaller RNA fragments that are 15 nucleotides or shorter.

As will be explained in greater detail below, the method may find particular use in analyzing samples that contain both "long" RNAs (such as mRNA, lncRNA, etc.) and small RNAs. After fragmentation, the RNA fragments may have a median size of at least 20 nucleotides, the small RNAs may have a median size in the range of 20 to 40 nucleotides and the shorter, undesirable, RNA fragments may be 15 nucleotides or shorter. The preference of polyA polymerase for longer substrates can be used to preferentially polyadenylate both the small RNAs and the longer RNA fragments, but not the smaller RNA fragments. The method may be employed on any RNA sample that comprises RNAs that are at least 40 nucleotides in length. The RNA molecules in such samples may have a median size of at least 40 nucleotides or at least 100 nucleotides, for example.

The present method, because it is capable of discriminating between RNA molecules that differ in length by only 5-10 nucleotides, is believed to provide higher resolution than other methods that physically remove smaller RNA fragments from the sample (e.g., by size exclusion chromatography and/or bead-based size selection).

BRIEF DESCRIPTION OF THE FIGURES

Some aspects of the present invention may be best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "RNA sample", as used herein, relates to a mixture of materials, typically, although not necessarily, in liquid form, e.g., In the form of an aqueous solution, containing one or more RNA molecules. An RNA sample may be obtained from cells, e.g., mammalian cells, for example. An RNA sample may contain any number of distinguishable RNA molecules. For example, in some embodiments, an RNA sample may contain a population of different RNA molecules, in which case it may contain more than 1,000, more than 10,000, more than 50,000, or more than 100,000 up to 1M or more different species of RNA, i.e., RNA molecules of different sequence. An RNA sample may contain long RNA molecules such as mRNA molecules, which are typically at least 100 nt in length (e.g., 200 nt to 10 kb in length) and have a median length in the range of 500-5,000 nt, as well as, for example, long intergenic noncoding RNAs (lincRNAs). An RNA sample may additionally contain a variety of small non-coding regulatory RNAs that may be generically referred herein to as "small RNAs", e.g., microRNAs, tiny non-coding RNAs, piwi-interacting small RNAs (piRNAs), small modulatory RNAs, and snoRNAs, etc. Small RNAs are typically below 100 nt in length and have a median length in the range of 20 nt to 40 nt. An RNA sample may additionally contain rRNA molecules, tRNA molecules, pre-miRNA molecules, and long non-coding RNA molecules such as large intergenic RNA (lincRNA) molecules. Unless otherwise indicated, an "RNA sample" may have any type of naturally-occurring RNA, including those described above and potentially others.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine, thymine and uracil (G, C, A, T, and U).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In some cases, an isolated substance may be dissolved in a liquid, e.g., an aqueous liquid. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography, sedimentation according to density, precipitation, solvent extraction and solid phase purification using a column or beads. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51 to 60, 61 to 70, 71 to 80, 80 to 100, 100 to 150 or 150 to 200, up to 500 nucleotides in length, for example. The term "duplex", "hybrid" or "double-stranded" as used herein refers to nucleic acids that have two strands that are bound together by based pairing.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions.

The terms "determining", "measuring", "evaluating", "assessing", "analyzing", and "assaying" are used interchangeably herein to refer to any form of measurement or analysis, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed, degraded or substantially reduced.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be of 5-50 bases, e.g., 10 to 30 bases, in length or longer depending on the application. An adaptor may contain a molecular barcode, restriction sites and/or primer binding sites, depending on the application. In the methods described below, at least the 3' end of the adaptor can be RNA. In some embodiments, an adaptor can contain a molecular barcode (e.g., an "index" or "indexing" sequence).

As used herein, the terms "3'-OH" and "3'-hydroxyl" refer to a nucleotide at the 3' terminus of a nucleic acid, where the nucleotide has a hydroxyl group at the 3' position.

As used herein, the term "5'-P" or "5'-phosphate" refers to a nucleotide at the 5' terminus of a nucleic acid, where the nucleotide has a phosphate group at the 5' position.

As used herein, the term "cDNA library" refers to a collection of DNAs, or library, synthesized from a template RNA and are therefore complimentary to the template RNA. The cDNA library can be sequenced, labeled, amplified and/or cloned, depending on how it is going to be used.

As used herein, the term "RNA:cDNA hybrid" refers to a product after first-strand cDNA synthesis catalyzed by reverse transcriptase using RNA as a template. An "RNA-cDNA hybrid" can be full-length if the cDNA portion includes the complete sequence of the 5'-ends of the template mRNA. RNA:DNA hybrids can also be made by hybridizing DNA oligonucleotides (which can be sequence-specific or random) with RNA.

As used herein, the term "template" refers to the substrate RNA for the reverse transcriptase to make cDNA. The template RNA is the target in a mixed population of RNA molecules for enrichment.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" or "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a composition, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "primer" refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase or a reverse transcriptase. Primers are generally of a length compatible with their use in synthesis of primer extension products, and are usually are in the range of between 6 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Primers are usually single-stranded. Primers have a 3' hydroxyl.

Figure 3:
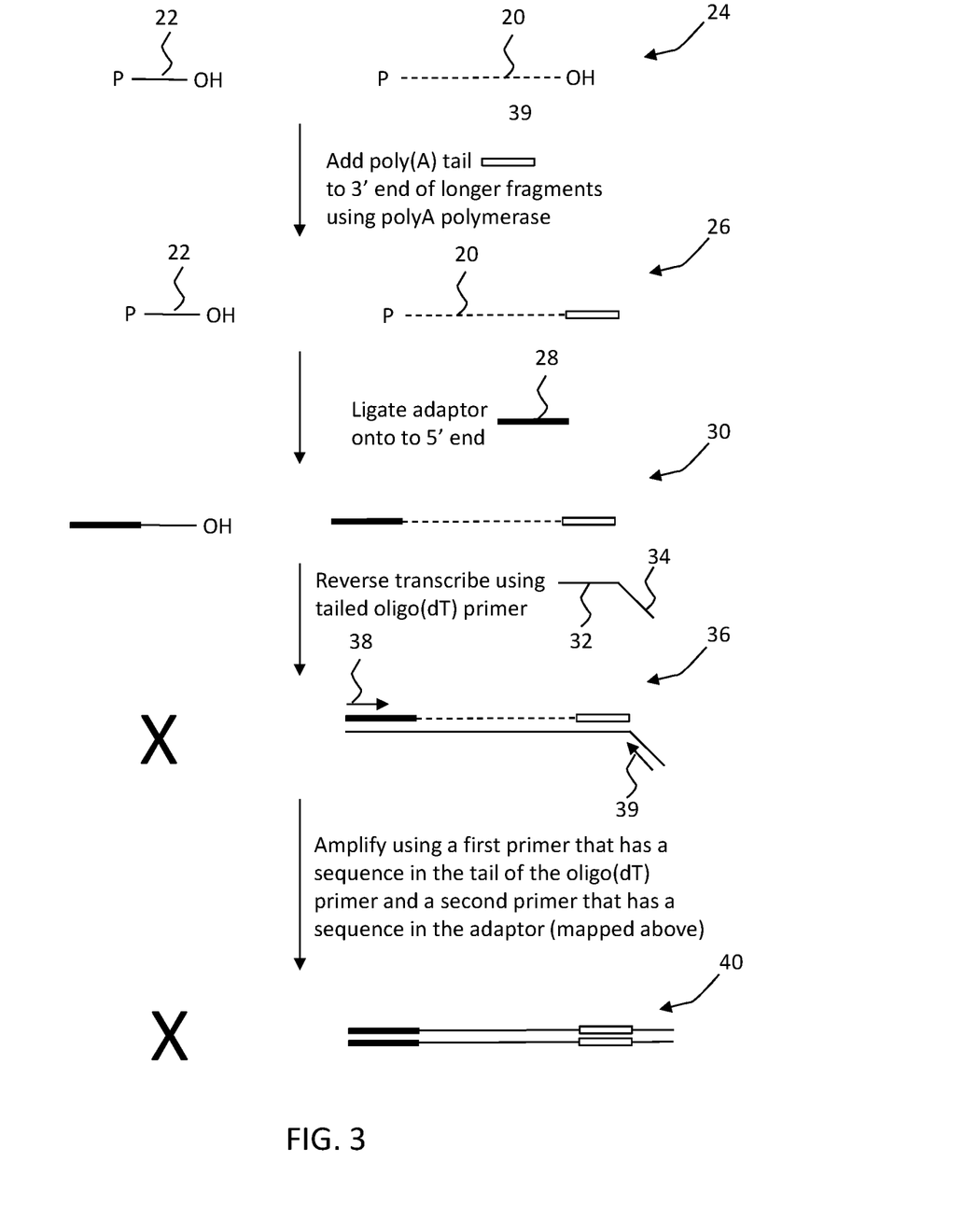
FIG. 3 schematically illustrates how shorter RNA fragments can be excluded from a cDNA library using the present method.

The term "oligo-dT primer" refers to a primer that is capable of priming cDNA synthesis from a polyA tail. With the possible exception of the last one or two nucleotides, an oligo-dT primer may have a 3' end sequence that has a string of thymines. Such a primer may have a 5' tail, as shown in FIG. 3. In some embodiments, oligo-dT primer may be anchored and may have the following sequence: TTTTTTTTTTTTTTTVN (SEQ ID NO:1), where V is G, A or C or analog thereof and N is any nucleotide or analog thereof. The T in such an oligonucleotide may be a T analog in that it is capable of specifically base pairing with an A.

The term "sequence-specific primer" for the purpose of reverse transcribing an RNA is intended to refer to a primer that hybridizes to a unique sequence in mRNA or a target RNA. Sequence-specific primers do not have a random sequence and are not made of a single nucleotide. Random primers and oligo(T) primers are not sequence specific primers.

The term "cDNA copy" refers to a DNA molecule that has the reverse complement of an RNA molecule (i.e., first strand cDNA) or a DNA molecule that has the same sequence as an RNA molecule except that the Us are T's (i.e., second strand cDNA). The RNA molecule can by any type of RNA, e.g., a small RNA, a fragment or mRNA, or a fragment of lncRNA, etc.

The term "reaction conditions" refers to the temperature of a reaction, the length of time the reaction is incubated for, and/or the components of the reaction (e.g., the amounts of salt, enzyme, pH, divalent cation used, enzyme inhibitors, etc.).

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 1:
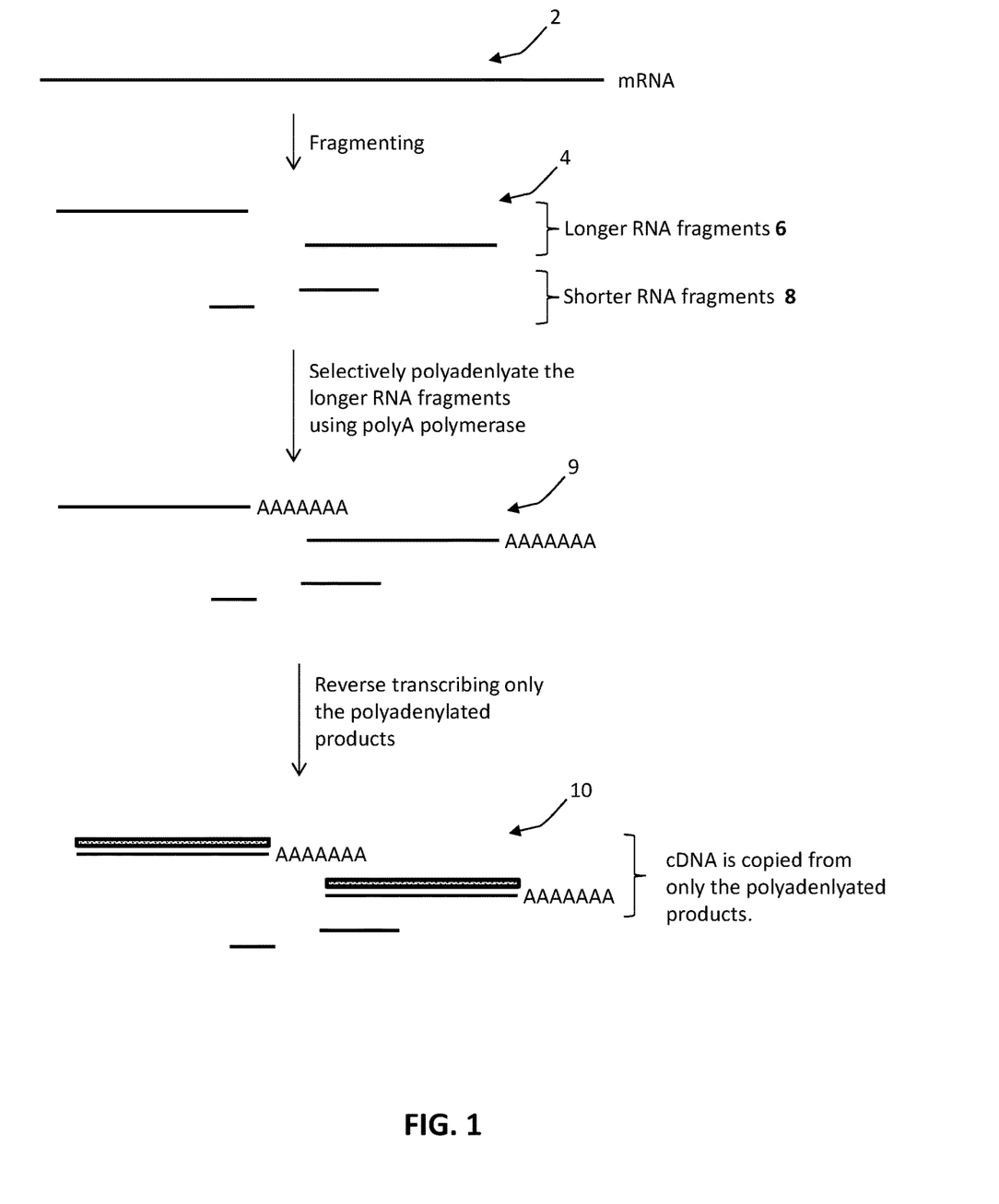
FIG. 1 schematically illustrates some of the principles of an embodiment of the present method.

FIG. 1 illustrates some of the principles of an embodiment of the method. With reference to FIG. 1, some embodiments of the method may comprise fragmenting a sample comprising mRNA, e.g., mRNA 2 to produce a population of RNA fragments 4 of different lengths, wherein the population of RNA fragments 4 comprises longer RNA fragments 6 and shorter RNA fragments 8. This fragmentation step may be done in a variety of different ways. For example (and as will be described in greater detail below), the RNA sample 2 may contain cDNA:mRNA hybrids (i.e., may comprise reverse transcription products primed using, e.g., an oligo(dT) primer), and the fragmenting of the mRNA may be done by treating the sample with RNAseH (see U.S. application Ser. No. 15/818,469, filed on Nov. 20, 2017, which is incorporated by reference herein). Fragmentation can also be done by hybridizing DNA oligonucleotides (which may be sequence-specific or random, for example) to the RNA to produce DNA:mRNA hybrids and then treating the hybrids with RNAseH. Alternatively, the mRNA may be fragmented by heating the mRNA (e.g., to a temperature of at least 60° C.) for a period of at least 5 minutes in the presence of a divalent cation (e.g., $Mg^{2+}$ or $Zn^{2+}$)) or another method (see, for example, Leven et al Nat Methods. 2010 7: 709-715). Depending on the fragmentation conditions used, the fragmentation step can result in longer fragments are at least 20 ribonucleotides in length and the shorter fragments 15 or less ribonucleotides in length. After the fragments have been made, then the longer fragments 6 are selectively adenylated using polyA polymerase to produce tailed RNA 9. Preferentially adding a polyA tail to the longer RNA fragments but not the shorter RNA fragments is done by incubating the population of RNA fragments 4 with a polyA polymerase under conditions wherein the polyA polymerase preferentially adds a polyA tail to the longer RNA fragments and not the shorter fragments, to produce tailed RNA 9. Suitable reaction conditions limit the activity of the polyA polymerase in the reaction. The activity that is effective for preferentially tailing only the longer fragments is generally much less than (e.g., at least $\frac{1}{10}^{th}$ of) the activity that typically used in a polyadenylation reaction. Under these conditions, the reaction is not believed to go to completion and the limited enzyme activity selects for the longer substrates. The activity of the enzyme can be limited in a variety of different ways. For example, in the present method the reaction conditions (i.e., the polyadenylation reaction buffer) may comprise polyA polymerase at a concentration of less than 0.02 U/uL (e.g., at a concentration of 0.002 U/uL to 0.02 U/uL or 0.003 U/uL to 0.015 U/uL of polyA), where unit of polyA polymerase is defined as the amount of enzyme that will incorporate 1 nmol of ATP into acid-insoluble material in 10 minutes at 37° C., in a reaction that contains the enzyme, a 15-mer RNA oligonucleotodie, 1× reaction buffer (50 mM Tris-HCl, 250 mM NaCl, 10 mM MgCl2, pH 7.9 @ 25° C.), 1 mM ATP, 2.5 mM MnCl2 and 3 H-ATP, analyzed using the method of Sambrook and Russell (Molecular Cloning, v3, 2001, pp. A8.25-A8.26). Typical polyadenylation reactions use polyA polymerase at a concentration of 0.333 U/uL to 0.5 U/uL and, as such, the present reaction may use less than $\frac{1}{20}^{th}$ of the concentration of polyA polymerase of a conventional reaction. For example, a 10 uL to 20 uL polyadenylation reaction may comprise less than 0.25 units of the polyA polymerase (e.g., 0.05 to 0.15 units of polyA polymerase). Typical polyadenylation reactions use 2-5 units of polyA polymerase. Alternatively, the activity of the polyA polymerase may be limited using a reduced amount of divalent cation in the reaction buffer. PolyA polymerase requires a divalent cation (typically $Mg^{2+}$) for activity and its activity can be attenuated in a reaction that has a decreased amount of divalent cation (e.g., $Mg^{2+}$). As such, in some embodiments, the reaction conditions (i.e., the polyadenylation reaction buffer) may comprise 0.6 mM to 1.2 mM (0.75 mM to 1.0 mM) of a divalent cation, e.g., $Mg^{2+}$, where a typical polyA tailing reaction may contain about 10 mM $Mg^{2+}$ (see the reaction conditions for determining a unit of polyA polymerase above). Typical reactions include an incubation for a time period of under 1 hour (e.g., 5 mins to 30 mins, up to 1 hr). The same effect can likely be created by altering other reaction conditions, e.g., the time or temperature of the incubation, or by manipulating other components of the reaction. A typical polyadenylation reaction may have 1 ng to 1 ug of fragmented RNA, but this may vary. For example, if one uses 1 ng of total RNA as an input into a fragmentation reaction that is targeted to polyA+ RNA, only a small fraction of the RNA, e.g., as low as 10 pg, may be fragmented.

After the tailed RNA 9 has been produced, the tailed RNA may be hybridized with an oligo(dT) oligonucleotide. After hybridization to the oligo(dT) oligonucleotide, the method may comprise reverse transcribing the tailed RNA using the oligo(dT) oligonucleotide as a primer to produce a cDNA library, or enriching for the tailed RNA by washing away RNA molecules that are not hybridized to the oligo(dT) oligonucleotide. In the latter embodiment, the tailed RNA 9 can be affinity selected using an oligo(dT) column, if desired. As shown in FIG. 1, after the tailed RNA 9 has been produced, the tailed RNA 9 may be reverse transcribed to produce a cDNA library 10. In some embodiments and as shown in FIG. 1, the tailed RNA 9 may be reverse transcribed using an oligo(dT) primer (e.g., an anchored oligo (dT) primer that may have a 5' tail). As illustrated in FIG. 1, only the polyadenylated RNAs (i.e., the polyadenylated RNAs but not the unpolyadenlyated RNAs) will be copied into cDNA because the oligo(dT) primer will only hybridize to the polyadenylated RNAs. The method shown in FIG. 1 therefore provides a way to preferentially make cDNA from longer RNAs. As shown, the method may be done without in the absence of a physical size selection step that involves incubating the RNA fragments 4 with a matrix that selectively binds to either the shorter RNA fragments or longer RNA fragments. However, a physical size selection step can be employed, if desired.

Figure 2:
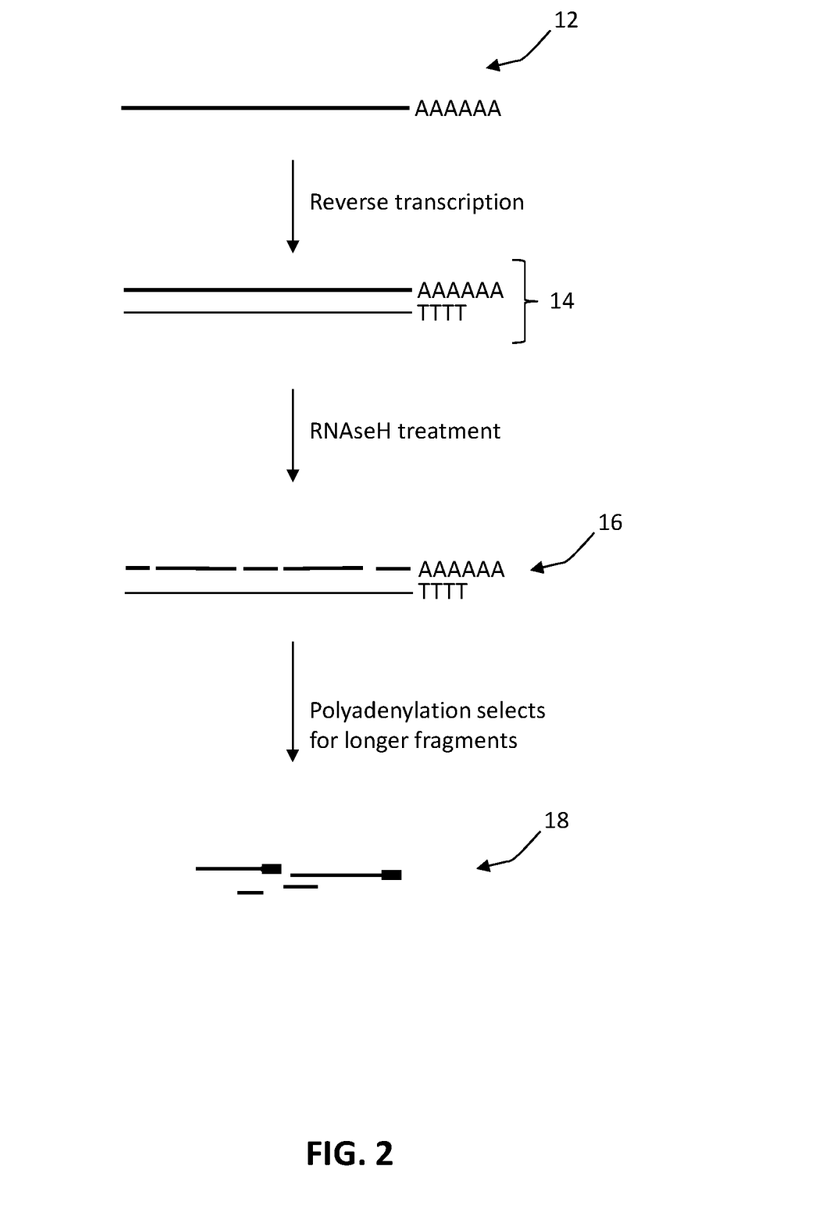
FIG. 2 schematically illustrates how fragmentation can be accomplished by RNAseH treatment of a DNA/RNA hybrid.

FIG. 2 illustrates an example of how fragments of RNA can be produced using RNaseH. It should be noted that the method shown in this figure is not the only method that can be used to make fragments of RNA. The method illustrated in FIG. 2 may comprise reverse transcribing RNA sample 12 that comprises polyA tailed mRNA to produce first strand cDNA product 14. The polyA tailed mRNA may be from a cell (e.g., a eukaryotic cell) or made by adding a polyA tail to a population of mRNAs that are not polyA tailed using polyA polymerase. As shown, the first strand cDNA product 14 comprises cDNA:RNA hybrids that comprise an RNA and a cDNA copy of the RNA. In the embodiment shown in FIG. 2, the reverse transcription may be primed using an oligo(dT) primer (e.g., an anchored oligo(dT) primer). In other embodiments, the initial reverse transcription step may be done using one more sequence-specific primers (e.g., primers that hybridize to unique sequences in the RNA) or random primers. Alternatively, the DNA:RNA hybrids may be made by hybridizing sequence-specific or random oligonucleotides to an RNA sample. The RNA sample may contain, for example, total cellular RNA, total RNA that has been depleted for one or more types of RNA (e.g., rRNA and/or tRNA), lncRNA, size-selected RNA or mRNA and small RNA, for example, although other combinations are contemplated. In some embodiments, the reverse transcription may be done by a "hot start" procedure in which two complementary mixtures are pre-heated to the incubation temperature prior to mixing them together. In these embodiments, the initial reverse transcription step may be done by: (i) pre-heating a first mixture comprising the primer and the RNA sample to a temperature in the range of 40-80 degrees, (ii) pre-heating a second mixture comprising the reverse transcriptase to a temperature in the range of 40-80 degrees, (iii) admixing the first and second mixtures to produce a reaction mix; and incubating the reaction mix at a temperature of 40-80 degrees for a sufficient time (e.g., at least 5 minutes), to produce the first strand cDNA product. As shown in FIG. 2, the method may comprise treating the first stand cDNA product 14 with RNAseH to produce a digested sample 16 that comprises fragments of the mRNA. In practice, the number fragments of mRNA per DNA:mRNA hybrid may vary greatly based on the length of the DNA: mRNA hybrids and the number of cleavage events that occur per DNA:mRNA hybrid (i.e., the number of times the RNAseH nicks the mRNA molecule of the DNA:mRNA hybrid). In some embodiments, at least 90% of the DNA: mRNA hybrids may give rise to approximately 4 to 200 DNA:mRNA hybrids each. The median length of fragments 14 may be at least 20 nucleotides (e.g., in the range of 20 to 100 or 20 to 50 nucleotides). As noted, the RNA may be fragmented using another method. Some of the alternative methods produce RNA fragments that have 5' hydroxyl and a 3' phosphate and, as such, may require a phosphatase and/or kinase treatment before moving on to the next step. mRNAs may be fragmented to a median length of between 10 to 200 nucleotides. In some embodiments, the median length of the fragments is 10-25 nucleotides. In other embodiments the median length may be 40-150 nucleotides. In either embodiment, there will be a substantial number of molecules that are 15 nucleotides or below in length, which can be eliminated using the present method.

In some embodiments, the reverse transcriptase and RNAseH activities required for the initial steps of the method are provided by different enzymes. In these embodiments, the reverse transcription step may be done using an RNAaseH⁻ reverse transcriptase, and the RNAseH treatment may be done using a separate enzyme. In some embodiments, the reverse transcription and/or the RNAseH may thermostable. In some embodiments, the initial reverse transcription step may be done at temperature in the range of 40° C. to 80° C. In some embodiments, the RNAseH treatment step may be done at a temperature in the range of 40° C. to 80° C., e.g., at a temperature in the range of 60° C. to 80° C. It is thought that at an elevated temperature incompletely digested mRNA fragments (e.g., fragments that have a median length in the range of 15 to 50 nucleotides) produced by RNAseH cleavage start to become disassociated from the cDNA to which they were bound. RNAseH requires a double-stranded substrate, and because their disassociation prevents the fragments from being a substrate for the RNAseH, mRNA fragments in the range of 15 to 50 nucleotides should not be digested any further, even in an extended incubation. Thus, in some embodiments, the reaction conditions (the salt concentration and temperature) can be adjusted to produce fragments of a pre-determined range of sizes. Higher salt and/or a higher incubation temperature should, in theory, result in a population of fragments that have a longer median length and lower salt and/or a lower incubation temperature should, in theory, result in a population of fragments that have a shorter median length. The length of the fragments can also be tailored by modifying the amount of enzyme used and/or the incubation conditions and/or by altering total RNA input concentration. In some embodiments, in order to avoid complete digestion of the mRNAs and to obtain mRNA fragments of the desired length, the amount of RNAseH used in the RNAseH treatment may be less than a tenth of the amount of RNAseH used for other reactions. For example, if 5 units of RNAseH are typically used to digest mRNA to completion, then 0.1 to 0.5 units of RNAseH (e.g., an amount in the range of 0.3 to 0.16 units) may be used in the present method, where one unit of RNaseH is the amount of enzyme which produces 1 nmol acid soluble ribonucleotides from [3H]poly(A)×poly(dT) in 20 minutes at 37° C. under the conditions used, using the method of Hillenbrand and Saudenbauer (Nucleic Acids Res. 1982 10:833).

Next and as shown in FIG. 2, the method may comprise polyadenylating the mRNA fragments to produce a cDNA library 18, using the method described in FIG. 1.

The polyadenylated fragments produced by the method shown in FIGS. 1 and 2 may be reverse transcribed using any suitable method. FIG. 3 shows one example of such a method although, as would be apparent, other methods may be used. For example, the 5' adaptor sequence may be added to the reverse transcription product by template switching, rather than ligation. In the example shown in FIG. 3, the method may comprise adding a poly(A) tail onto the 3' end of the longer RNA fragments 20 but not the shorter RNA fragments 22 of a sample 24 using an polyA polymerase, as described above, to produce tailed RNA 26. As shown, the longer fragments 20 have an A tail whereas the shorter fragments 22 do not have an A tail in tailed RNA 26. Next, the fragments may be reverse transcribed by ligating a 5' adaptor 28 to the tailed fragments (and the untailed fragments), to produce an adaptor-tagged sample 30. In some embodiments the 5' adaptor may be a single-stranded oligonucleotide in the range of 5 to 20 nt in length (e.g., 6, 7, 8, 9, 10, 11 or 12 nt in length), although adaptors having a length outside of this range may also be employed. The adaptor may be an RNA oligonucleotide, a DNA oligonucleotide or an oligonucleotide that comprises DNA and RNA. The adaptor may be ligated onto the RNA molecules of the digested sample using an RNA ligase, e.g., T4 RNA ligase, using any of the methods outlined in Wang et al (RNA 2007 13: 151-159) or Lockhart et al (U.S. Pat. No. 6,344,316) among many others. The RNA ligase used in the method can be any suitable ligase. In some embodiments, T4 RNA ligase can be used, although a variety of other RNA ligases that have a preference for single-stranded substrates can be used instead. In some embodiments, the RNA ligase used may be thermostable. In these embodiments, the ligation reaction may be done at an elevated temperature that may be in the range of 40 to 80° C.

The longer fragments in the A-tailed, adaptor ligated sample 30 may be reverse transcribed using an oligo(dT) primer 32 (e.g., an anchored oligo(dT) primer) to produce cDNA library 36. In the embodiment shown, oligo(dT) primer 32 contains an optional 5' tail 34, which does not hybridize to the A-tailed, adaptor ligated RNAs 30. As shown in FIG. 3, the cDNA library 36 may be optionally amplified by PCR to produce an amplification product 40. This step may be done using a first primer 38 that has a 3' end that is the same as a sequence in the 5' adaptor and a second primer 39 that has a 3' end that is the same as a sequence in the tail of the oligo(dT) primer. As shown, the amplification product 40 contains amplicons of the longer RNA fragments but not the shorter RNA fragments. In some embodiments, the amplification product may be subjected to a size selection step to remove unincorporated primers and/or unwanted species such as rRNA fragments or snoRNAs prior to analysis.

In some embodiments that use RNAseH to fragment the RNA, the cDNA that is made in the first step of the method is not itself analyzed and, as such, the cDNA molecules made in the initial step of the method may be degraded (e.g., using a DNAse treatment), discarded (e.g., purified away from the cDNA in the library by size separation) and/or diluted out (by preferentially amplifying the cDNA molecules in the cDNA library) prior to sequencing.

In some embodiments, the initial sample (prior to fragmentation) may comprise small RNAs that are in the range 20 and 50 nucleotides in length and have a median length in the range of 20 nt to 40 nt, in addition to mRNA. Small RNAs include microRNA (miRNA) molecules, tiny noncoding RNA (tncRNA) molecules and small modulatory RNA (smRNA) molecules, as well as others. In these embodiments, the initial fragmentation step may avoid fragmenting the small RNAs. For example, if the initial RNA is fragmented by heat in the presence of a divalent cation (which primarily cleaves longer RNAs because they contain more cleavage sites than short RNAs), then the cleavage reaction can be terminated before the small RNAs are significantly fragmented. In other cases, cleavage of the small RNAs can be avoided because they do not contain a polyA tail. Specifically, if the fragmenting is done using the method illustrated in FIG. 2, then the small RNAs should not be fragmented because they do not have a polyA tail and will not be copied into cDNA in the initial reverse transcription step. RNAseH requires an DNA:RNA hybrid and, as such, only the RNAs that have been reverse transcribed (and not the small RNAs or other types of RNA that have not been reverse transcribed) should be cleaved by the RNAseH. If small RNAs are present in the sample, then the RNAs may be fragmented to a median length that is similar to the length of the small RNAs. Small RNAs can be in the range of 20-29 nucleotides in length, and many small RNAs are approximately 20-25 nucleotides in length. As such, if small RNAs and longer RNAs (e.g., mRNAs and lncRNAs) are going to be analyzed, then the RNAs may be fragmented to a median length of between 10 to 100 nucleotides, e.g., 15 to 50 nucleotides. As such, in some embodiments, the method may comprise fragmenting the sample to produce a population of RNA fragments of different lengths, wherein the population of RNA fragments comprises: i. longer RNAs comprising unfragmented small RNAs and fragments of the mRNA and ii. shorter RNAs comprising fragments of the mRNA, adding a polyA tail to the longer RNAs but not the shorter RNAs by incubating the population of RNA fragments with a polyA polymerase under suitable reaction conditions (as described above), to produce tailed RNA that contains tailed RNA fragments and tailed unfragmented small RNAs; (c) hybridizing the tailed RNA to an oligo(dT) oligonucleotide; and (d) reverse transcribing the tailed RNA using the oligo(dT) oligonucleotide as a primer, to produce a cDNA library or enriching for the tailed RNA by washing away RNA molecules that are not hybridized to the oligo (dT) oligonucleotide. For example, in some embodiments, the method may comprise reverse transcribing the tailed RNA to produce a cDNA library that comprises: i. copies of the small RNAs and ii. copies of the longer RNA fragments. In these embodiments, both the small RNAs and the RNA fragments have a 5' phosphate and a 3' hydroxyl and, as such, can be polyadenylated, ligated to adaptors, and reverse transcribed together in the same reaction (e.g., by polyadenylating the 3' end of any longer RNAs using poly A polymerase, as discussed above, ligating a 5' adaptor to any RNA molecules that have a 5' phosphate, and reverse transcribing any molecules that have been tailed using an oligo(dT) primer, for example). The cDNA library may contain the first strand cDNA made in the initial step of the method, or not. In some cases, the first strand cDNA made in the initial step of the method may have been removed or degraded prior to making the cDNA library. This embodiment of the method provides a way to analyze small RNAs and mRNA in the same workflow.

In embodiments in which the cDNAs are sequenced, the cDNA library may be amplified using one or more primers that hybridize to the added sequences (or their complements), as described above. In some embodiments, the primers used may have sequences that are compatible with the sequencing platform being used (e.g., P5 and P7 sequences, which sequences are compatible with Illumina's sequencing platform) and the amplification products will have those sequences at their ends (e.g., P5 sequence at one and the P7 sequence at the other, if the Illumina sequencing platform is being used).

The sequencing step may be done using any convenient next generation sequencing method and may result in at least 10,000, at least 50,000, at least 100,000, at least 500,000, at least 1M, at least 10M, at least 100M, 1B or at least 10B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

In certain embodiments, the cDNA that is sequenced may comprise a pool of cDNA libraries made from a plurality of different RNA samples, wherein the different cDNA libraries have a molecular barcode (in the adaptor or PCR primers) to indicate their source. In some embodiments the cDNAs being analyzed may be derived from a single source (e.g., a single organism, virus, tissue, cell, subject, etc.), whereas in other embodiments, the cDNAs that are sequenced may be a pool of nucleic acids extracted from a plurality of sources (e.g., a pool of nucleic acids from a plurality of organisms, tissues, cells, subjects, etc.), where by "plurality" is meant two or more. As such, in certain embodiments, cDNAs that are sequenced can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. The sequence reads may be analyzed by a computer and, as such, instructions for performing the steps set forth below may be set forth as programming that may be recorded in a suitable physical computer readable storage medium.

The method described herein can be employed to analyze mRNA and, optionally, small RNAs from virtually any organism and/or sample-type, including, but not limited to, plants, animals (e.g., reptiles, mammals, insects, worms, fish, etc.), tissue samples, cadaveric tissue, archaeological/ancient samples, etc. In certain embodiments, the RNA sample used in the method may be derived from a mammal, where in certain embodiments the mammal is a human. In exemplary embodiments, the RNA sample may contain RNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the RNA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cfRNA obtained from blood, e.g., from the blood of a pregnant female or a patient.

The present method may be employed in a variety of diagnostic, drug discovery, and research applications that include, but are not limited to, diagnosis or monitoring of a disease or condition (where the expression of an mRNA and/or small RNA provides a marker for the disease or condition), discovery of drug targets (where an mRNA and/or small RNA is differentially expressed in a disease or condition and may be targeted for drug therapy), drug screening (where the effects of a drug are monitored by assessing the level of an mRNA and/or small RNA), determining drug susceptibility (where drug susceptibility is associated with a particular profile of an mRNA and/or small RNA) and basic research (where is it desirable to identify the presence of an mRNA and/or small RNA in a sample, or, in certain embodiments, the relative levels of a particular mRNA and/or small RNA in two or more samples).

In certain embodiments, relative levels of an mRNA and/or small RNA in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the mRNA and/or small RNA profiles of two or more different samples may be compared to identify mRNAs and/or small RNAs that are associated with a particular disease or condition (e.g., an mRNA and/or small RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., a normal cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient;

cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

In some embodiments, the sequence reads may be analyzed to provide a quantitative determination of which sequences are in the sample. This may be done by, e.g., counting sequence reads or, alternatively, counting the number of original starting molecules, prior to amplification, based on their fragmentation breakpoint and/or whether they contain the same indexer sequence (which can be present in the 5' adaptor, for example). The use of molecular barcodes in conjunction with other features of the fragments (e.g., the end sequences of the fragments, which define the breakpoints) to distinguish between the fragments is known. Molecular barcodes and exemplary methods for counting individual molecules are described in Casbon (Nucl. Acids Res. 2011, 22 e81) and Fu et al (Proc Natl Acad Sci USA. 2011 108: 9026-31), among others. Molecular barcodes are described in US 2015/0044687, US 2015/0024950, US 2014/0227705, U.S. Pat. Nos. 8,835,358 and 7,537,897, as well as a variety of other publications.

Also provided is a method for identifying a pattern that correlates with phenotype, e.g., a disease, condition or clinical outcome, etc. In some embodiments, this method may comprise (a) performing the above-described method on a plurality of RNA samples, wherein the RNA samples are isolated from patients having a known phenotype, e.g., disease, condition or clinical outcome, thereby determining which RNAs from each of the patients; and (b) identifying a signature that is correlated with the phenotype.

In some embodiments, the signature may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

Also provided is a method for analyzing a patient sample. In this embodiment, the method may comprise: (a) identifying, using the above-described method, sequences that are under and/or over expressed in a patient; (b) comparing the identified sequences to a set of signature sequences that are correlated with a phenotype, e.g., a disease, condition, or clinical outcome etc.; and (c) providing a report indication a correlation with phenotype. This embodiment may further comprise making a diagnosis, prognosis or theranosis based on the results of the comparison.

In some embodiments, the method may involve creating a report (an electronic form of which may have been forwarded from a remote location) and forwarding the report to a doctor or other medical professional to determine whether a patient has a phenotype (e.g., cancer, etc.) or to identify a suitable therapy for the patient. The report may be used as a diagnostic to determine whether the subject has a disease or condition, e.g., a cancer. In certain embodiments, the method may be used to determine the stage or type cancer, to identify metastasized cells, or to monitor a patient's response to a treatment, for example.

In any embodiment, a report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the report may be analyzed by an MD or other qualified medical professional, and a report based on the results of the analysis of the image may be forwarded to the patient from which the sample was obtained.

Accordingly, among other things, the instant methods may be used to link the expression of certain genes to certain physiological events.

EMBODIMENTS

Embodiment 1

A method for processing an RNA sample, comprising, (a) fragmenting a sample comprising RNA to produce a population of RNA fragments of different lengths, wherein the population of RNA fragments comprises longer RNA fragments and shorter RNA fragments, (b) incubating the population of RNA fragments with a polyA polymerase under conditions wherein the polyA polymerase preferentially adds a polyA tail to the longer RNA fragments and not the shorter fragments, to produce tailed RNA;

(c) hybridizing the tailed RNA to an oligo(dT) oligonucleotide; and (d) either (i) reverse transcribing the tailed RNA using the oligo(dT) oligonucleotide as a primer, to produce a cDNA library or (ii) enriching for the tailed RNA by washing away RNA molecules that are not hybridized to the oligo(dT) oligonucleotide.

Embodiment 2

The method of claim 1, wherein the RNA sample comprises at least mRNA.

Embodiment 3

The method of any prior claim, wherein the longer fragments are at least 20 ribonucleotides in length and the shorter fragments up to 15 ribonucleotides in length.

Embodiment 4

The method of any prior claim, wherein the conditions of step (b) comprise 0.6 mM to 1.2 mM of a divalent cation.

Embodiment 5

The method of any prior claim, wherein the conditions of step (b) comprise 0.75 mM to 1.0 mM of a divalent cation.

Embodiment 6

The method of claim 4 or 5, wherein the divalent cation is $Mg^{2+}$.

Embodiment 7

The method of any of claims 1-3, wherein the conditions of step (b) comprise polyA polymerase at a concentration of less than 0.02 U/uL.

Embodiment 8

The method of any of claims 1-3, wherein the conditions of step (b) comprise polyA polymerase at a concentration in the range of 0.002 U/uL to 0.02 U/uL.

Embodiment 9

The method of any prior claim, wherein the sample of step (a) comprises DNA:RNA hybrids, and the method comprises treating the sample with RNAseH.

Embodiment 10

The method of any of claims 1-8, wherein step (a) is done by heating the RNA in the presence of a divalent cation.

Embodiment 11A

The method of any prior claim, wherein the sample of step (a) further comprises small RNAs, wherein: the population of RNA fragments of step (a) comprises: i. longer RNAs comprising unfragmented small RNAs and fragments of the RNA and ii. shorter RNAs comprising fragments of the RNA, the tailed RNA of step (b) contains tailed RNA fragments and tailed unfragmented small RNAs.

Embodiment 11B

The method of any prior claim, wherein the sample of step (a) further comprises small RNAs, wherein the method comprises:

(a) fragmenting the sample to produce a population of RNA fragments of different lengths, wherein the population of RNA fragments comprises: i. longer RNAs comprising unfragmented small RNAs and fragments of the RNA and ii. shorter RNAs comprising fragments of the RNA, (b) incubating the population of RNA fragments with a polyA polymerase under conditions wherein the polyA polymerase preferentially adds a polyA tail to the longer RNAs and not the shorter RNAs, to produce tailed RNA that contains tailed RNA fragments and tailed unfragmented small RNAs; and (c) hybridizing the tailed RNA to an oligo(dT) oligonucleotide; and (d) reverse transcribing the tailed RNA using the oligo (dT) oligonucleotide as a primer, to produce a cDNA library or enriching for the tailed RNA by washing away RNA molecules that are not hybridized to the oligo(dT) oligonucleotide.

Embodiment 12

The method of claim 11, wherein the small RNAs include microRNA (miRNA) molecules, tiny non-coding RNA (tncRNA) molecules, small modulatory RNA (smRNA) molecules, Piwi-interacting RNA (pRNA) molecules, and snoRNA molecules.

Embodiment 13

The method of any prior claim, further comprising sequencing the cDNA library or the enriched tailed RNA.

Embodiment 14

The method of claim 13, wherein the method comprises amplifying the cDNA library by PCR, prior to sequencing.

Embodiment 15

The method of any prior claim, wherein the method further comprises adding an adaptor sequence to the 5' end of the population of RNA fragments of (a) or the tailed RNA of (b).

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

Except for changes to the polyadenylation step, a total of 20 ng MCF7 total RNA was fragmented, polyadenylated, ligated to adaptors, reverse transcribed and amplified essentially as described in U.S. patent application Ser. No. 15/818,469, filed on Nov. 20, 2017, and incorporated by reference herein. Libraries were sequenced on an Illumina MiSeq. Fastq files were generated and reads were trimmed using cutadapt then aligned to a human transcriptome reference. Samtools was used to count mRNA-aligned reads at each insert length.

In the first experiment, different amounts of poly(A) polymerase were added to the polyadenylation reaction. In this experiment, the polyadenylation reaction of condition A (15 uL) contains 1 uL of undiluted poly(A) polymerase (5

U/uL) and 10 mM $MgCl_2$ in a 1× buffer, whereas the polyadenylation reaction in condition B (15 ul) contains 1 ul of a 1/48 dilution of poly(A) polymerase (5 U/uL, diluted in its enzyme storage buffer) and 10 mM $MgCl_2$ in a 1× buffer. The final concentration of the enzyme in condition A is approximately 0.33 U/uL whereas the final concentration of the enzyme in condition B is approximately 0.007 U/uL. In total, condition A uses 5 U of the enzyme and condition B uses approximately 0.10 U of the enzyme.

Figure 4:
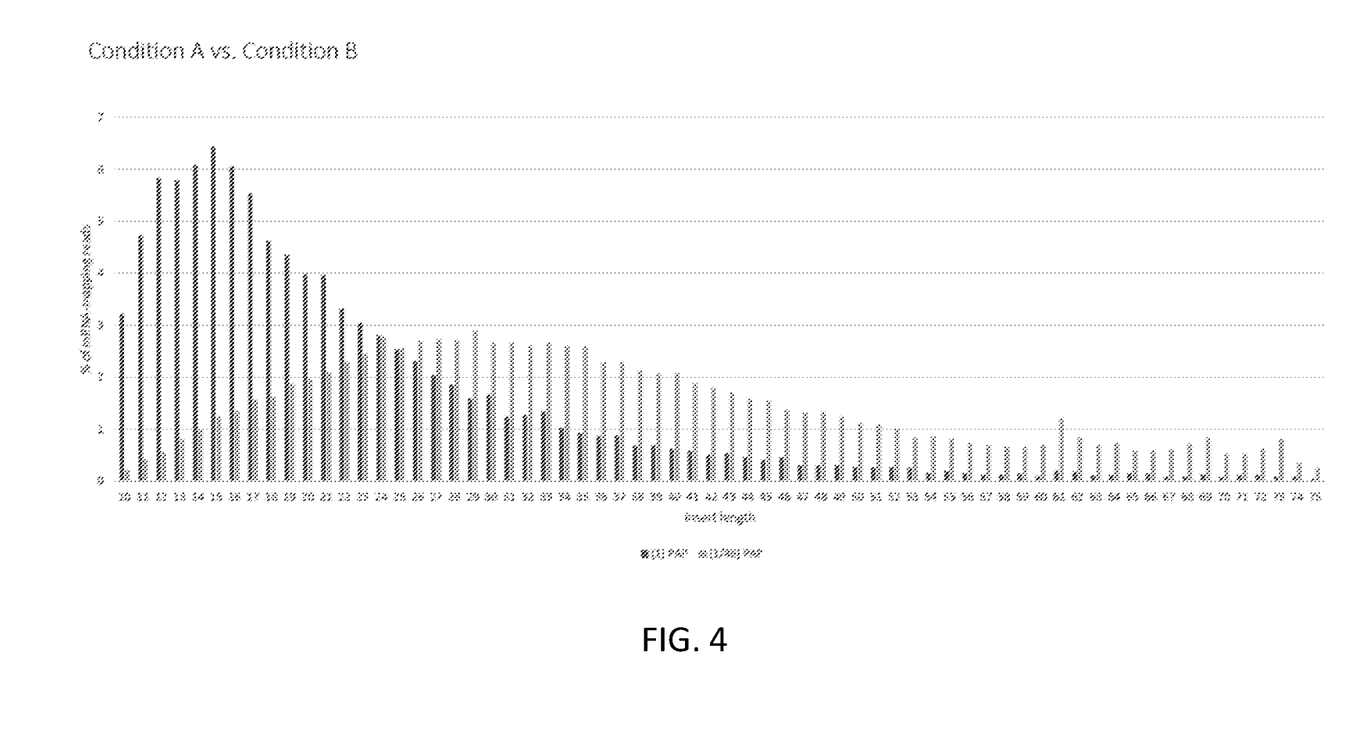
FIG. 4 is a bar graph showing data from the first experiment, as described in the examples.

The results of the first experiment are shown in FIG. 4. These results show that that there is much less bias towards shorter sequence reads (i.e., reads for shorter fragments) if a 1/48 dilution of the poly(A) polymerase is used.

In the second experiment, the polyadenylation reaction was done using different amounts of $MgCl_2$. $MgCl_2$ is required for poly(A) polymerase and reducing the amount of $MgCl_2$ decreases the activity of the enzyme. In this experiment, the polyadenylation reaction in condition C contains 1 ul of undiluted poly(A) polymerase and 10 mM $MgCl_2$ in a 1× reaction, whereas the polyadenylation reaction in condition D contains 1 ul of undiluted poly(A) polymerase and 1 mM $MgCl_2$ in a 1× reaction.

Figure 5:
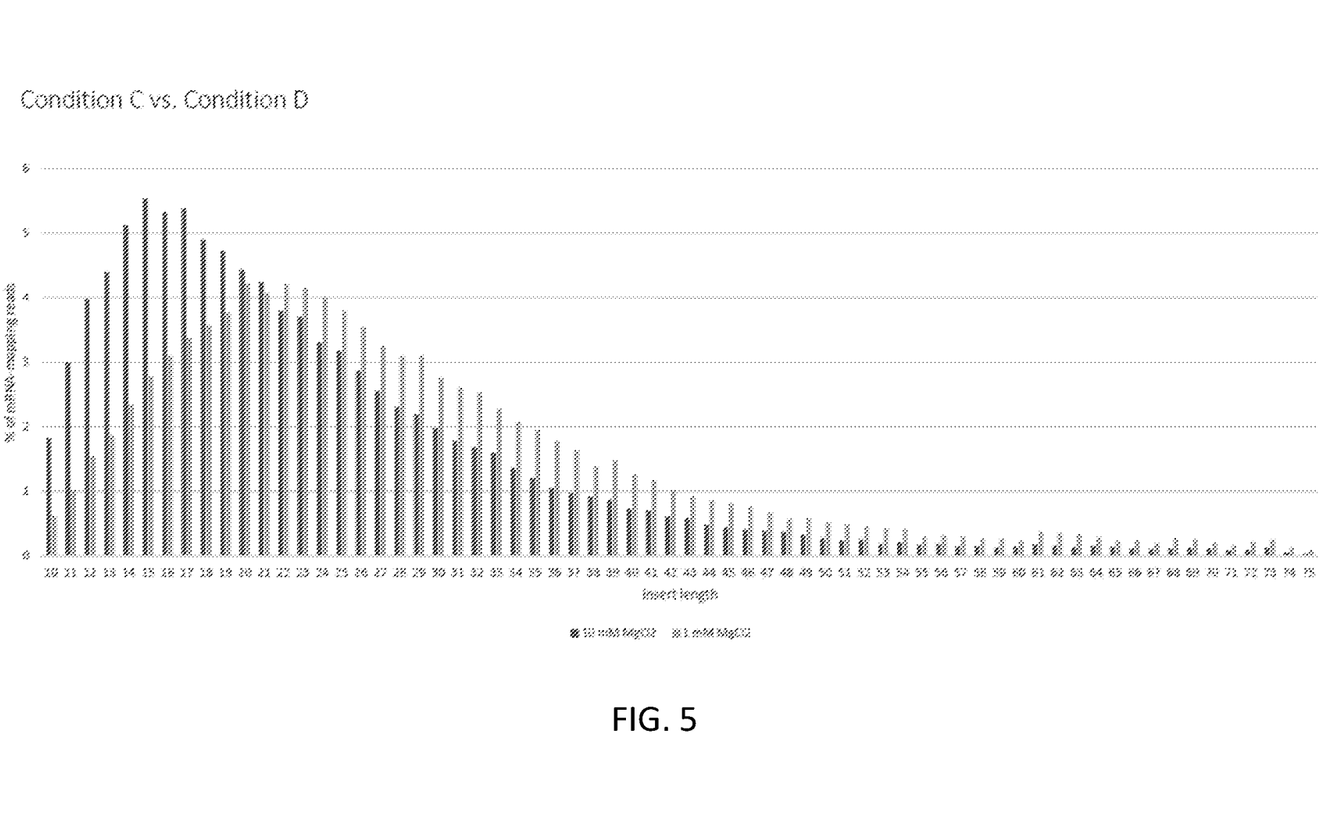
FIG. 5 is a bar graph showing data from the second experiment, as described in the examples.

The results of the second experiment are shown in FIG. 5. These results show that that there is much less bias towards shorter sequence reads (i.e., reads for shorter fragments) if the polyadenylation reaction is done in a reaction buffer that contains 1 mM $MgCl_2$.

2. The method of claim 1, wherein the RNA sample comprises at least mRNA.

3. The method of claim 1, wherein the longer fragments are at least 20 ribonucleotides in length and the shorter fragments up to 15 ribonucleotides in length.

4. The method of claim 1, wherein the conditions of (b) comprise 0.6 mM to 1.2 mM of a divalent cation.

5. The method of claim 1, wherein the conditions of (b) comprise 0.75 mM to 1.0 mM of a divalent cation.

6. The method of claim 4, wherein the divalent cation is $Mg^{2+}$.

7. The method of claim 1, wherein the conditions of (b) comprise polyA polymerase at a concentration of less than 0.02 U/uL.

8. The method of claim 1, wherein the conditions of (b) comprise polyA polymerase at a concentration in the range of 0.002 U/uL to 0.02 U/uL.

9. The method of claim 1, wherein the sample of (a) comprises DNA:RNA hybrids, and the method comprises treating the sample with RNAseH.

10. The method of claim 1, wherein (a) is done by heating the RNA in the presence of a divalent cation.

11. The method of claim 1, wherein the RNA sample further comprises small RNAs, and:
 the mixture of RNA fragments produced in (a) comprises:
  the small RNAs and the longer RNA fragments, and

That which is claimed is:

1. A method for processing an RNA sample, comprising,
 (a) fragmenting a sample comprising RNA to produce a mixture of RNA fragments of different lengths, wherein the mixture of RNA fragments comprises longer RNA fragments and shorter RNA fragments,
 (b) incubating the mixture of RNA fragments with a polyA polymerase under conditions wherein the polyA polymerase preferentially adds a polyA tail to the longer RNA fragments and not the shorter fragments, to produce tailed RNA;
 (c) hybridizing the tailed RNA to an oligo(dT) oligonucleotide; and
 (d) either (i) reverse transcribing the tailed RNA using the oligo(dT) oligonucleotide as a primer, to produce a cDNA library or (ii) enriching for the tailed RNA by washing away RNA molecules that are not hybridized to the oligo(dT) oligonucleotide.

the tailed RNA produced in (b) comprises tailed longer RNA fragments and tailed small RNAs.

12. The method of claim 11, wherein the small RNAs include microRNA (miRNA) molecules, tiny non-coding RNA (tncRNA) molecules, small modulatory RNA (smRNA) molecules, Piwi-interacting RNA (pRNA) molecules, and snoRNA molecules.

13. The method of claim 1, further comprising sequencing the cDNA library or the enriched tailed RNA.

14. The method of claim 13, wherein the method comprises amplifying the cDNA library by PCR, prior to sequencing.

15. The method of claim 1, wherein the method further comprises
 adding an adaptor sequence to the 5' end of the mixture of RNA fragments of (a) or the tailed RNA of (b).

\* \* \* \* \*